United States Patent [19]

Manghisi et al.

[11] 4,046,762
[45] Sept. 6, 1977

[54] ESTERS AND AMIDES OF 3-ARYL-1,4 BENZODIOXAN-2-CARBOXYLIC ACIDS

[75] Inventors: Elso Manghisi, Monza; Aldo Salimbeni, Milan, both of Italy

[73] Assignee: Instituto Luso Farmaco D'Italia S.r.l., Milan, Italy

[21] Appl. No.: 407,109

[22] Filed: Oct. 17, 1973

[30] Foreign Application Priority Data

Oct. 20, 1972 Italy .................................. 30778/72

[51] Int. Cl.$^2$ .......................................... C07D 295/00
[52] U.S. Cl. ............................ 544/148; 260/268 BC; 260/268 TR; 260/293.58; 260/308 R; 260/326.36; 260/340.3; 424/249; 424/248.55; 544/58
[58] Field of Search ...................... 260/247.2 B, 340.3, 260/293.58, 326.36, 308, 268 BC, 268 TR

[56] References Cited
FOREIGN PATENT DOCUMENTS 1,312,893  11/1962  France ........................... 260/247.2 B

OTHER PUBLICATIONS

Yen, H. C. Y. et al., Inter. J. of Neuropharmacol., 1964, 2, 337-347.

*Primary Examiner*—Paul J. Killos
*Attorney, Agent, or Firm*—Flynn & Frishauf

[57] ABSTRACT

1,4-Benzodioxan derivatives of the formula:

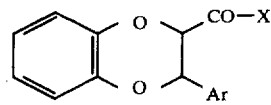

in which Ar is an aryl group and X is —OR, where R is hydroxyalkyl, aminoalkyl, or aminoalkoxyalkyl, or

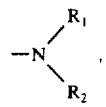

where $R_1$ and $R_2$ are hydrogen, hydroxyl, alkyl, aryl, or aralkyl or are joined together to form an alkylene group which may contain an oxygen, sulphur or nitrogen hetero atom, have interesting pharmacological properties.

5 Claims, No Drawings

ESTERS AND AMIDES OF 3-ARYL-1,4 BENZODIOXAN-2-CARBOXYLIC ACIDS

This invention provides the compounds of formula:

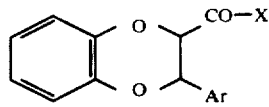
(I)

in which: Ar represents a monocarbocyclic, substituted or unsubstituted aryl group such as phenyl or substituted phenyl which may have one or more identical or different substituents, e.g. lower alkyl, for example methyl, ethyl, n-propyl, or isopropyl, lower alkoxy, for example methoxy, ethoxy, n-ipropyloxy, isoproploxy, or n-butyloxy, halogen, for example fluorine, chlorine, or bromine, trifluoromethyl X represents either (a) an OR group, in which R is hydroxyalkyl, for example 2-hydroxyethyl, 3-hydroxypropyl, or 2,3-dihydroxypropyl, ω-aminoalkyl, for example 2-diethylaminoethyl, 2-morpholino-ethyl, or 2-piperidinoethyl, or ω-aminoalkoxyalkyl, for example 2-diethylaminoethoxyethyl 2-morpholinoethoxyethyl, or 2-piperidino-ethoxyethyl, or (b) an

group in which $R_1$ and $R_2$, identical or different, are hydrogen, hydroxy, lower alkyl, or carbocyclic monocyclic aryl, especially phenyl, or lower monocarbocyclic arylalkyl groups, especially phenylalkyl, or the substituents $R_1$ and $R_2$ are joined together to form an N,N-alkyleneimino group, an N,N-oxoalkyleneimino group, an N,N-thiolkyleneimino group or an N,N-azaalkyleneimino group, in which the alkylene has three to eight carbon atoms, and the aza-nitrogen may be substituted. The

group may thus be an N-monosubstituted amino group, such as N-alkylamino, for example methylamino, ethylamino, or N-propylamino, N-cycloalkylamino, for example N-cyclohexylamino, N-arylalkylamino, for example benzylamino, N-dialkylaminoethylamino, for example N,N-diethylethylenediamino, N-arylamino, for example N-phenylamino or substituted N-phenylamino, an N,N-disubstituted amino group such as N,N-dialkylamino, for example N,N-dimethylamino, N-methyl-N-ethylamino, N,N-diethylamino, N,N-di-n-propylamino, or N,N-diisopropylamino, or a cyclic group such as 1-pyrrolidinyl, 1-piperidinyl, 2-methyl-1-piperidinyl, 4-hydroxy-4-phenyl-1-piperidinyl, 4-hydroxy-4-p-chlorophenyl-1-piperidinyl, 4-carboxyamino-4-phenyl-1-piperidinyl, 4-benzoylamino-1-piperidinyl, 4-p-fluorobenzoyl-1-piperidinyl, 1-N,N-(1,6-hexylene)imino, 1-N,N-(1,7-heptylene)imino, 4-morpholinyl, 4-thiomorpholinyl, or an N,N-azaalkylene-imino in which the alkylene has from 4 to 6 carbon atoms and in which the "aza" nitrogen is substituted by lower alkyl, for example methyl, ethyl, or propyl, lower hydroxyalkyl, for example hydroxyethyl, lower arylalkyl, for example benzyl or 2-phenylethyl, or monocarbocyclic aryl, preferably phenyl, substituted or unsubstituted by halogen, alkyl, or lower alkoxy, for example phenyl, 2-tolyl, 2,3-xylyl, 4-chlorophenyl, or 2-methoxyphenyl, such as, in particular 1-piperazinyl, 4-methyl-1-piperazinyl, 4-ethyl-1-piperazinyl, 4-(2-hydroxyethyl)-1-piperazinyl, 4-phenyl-1-piperazinyl, 4-p-chlorophenyl-1-piperazinyl, or 4-2'-methoxy-phenyl-1-piperazinyl.

The invention includes within its scope the salts of the compounds of formula I with pharmaceutically acceptable inorganic acids, for example hydrochloric, hydrobromic, nitric, sulphuric, and phosphoric acid, organic carboxylic acids, for example acetic, propionic, glycolic, malonic, succinic, maleic, hydroxymaleic, fumaric, malic, tartaric, citric, glucuronic, benzoic, mandelic, salicylic, 4-aminosalicylic, 2-phenoxybenzoic, 2-acetoxy benzoic, pamoic, bicotinic, and isonicotinic acid, and organic sulphonic acids, for example methanesulphonic, ethanesulphonic, 2-hydroxyethanesulphonic, ethane-1,2-disulphonic, p-toluenesulphonic, and naphthalene-2-sulphonic acid. Mono or poly salts are formed according to the number of malifiable groups present in the molecules.

The invention also provides processes for preparing the compounds of formula (I). According to one process, the compounds are obtained by reacting a carboxylic acid of the formula:

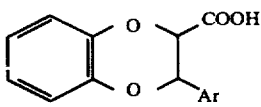
(II)

in which Ar is as hereinbefore defined, or a suitable derivative thereof, for example an ester (for example a methyl, ethyl, or benzyl ester), a halide (such as the chloride or bromide), or a mixed anhydride with a lower aliphatic acid (such as acetic or propionic acid), with an alcohol of the formula:

R—OH (III)

in which R is as hereinbefore defined, or with an amine of the formula:

(IV)

in which $R_1$ and $R_2$ are as hereinbefore defined.

The reaction between an ester of formula II (for example an ethyl ester) and an alcohol or formula III can be conducted by suspending the reagents in a hydrocarbon solvent (such as pentane or heptane) and heating to boiling point in the presence of a basic catalyst such as sodium ethylate, the ethanol or other alcohol produced in the reaction being removed as an azeotropic mixture with the solvent used. If however the ester of formula II is reacted with an amine of formula IV it is convenient to operate at a temperature between 100° and 200° C with an excess of the amine and in the presence of traces of sodium metal.

The reaction between a halide of the acid of formula II and an alcohol of formula III or an amine of formula IV is conducted in an apolar solvent such as benzene or toluene, heating to boiling point, using as hydrogen halide acceptor a tertiary base (such as triethylamine or pyridine) or an excess of the amine itself or of the alcohol if this contains a basic group.

The compounds of formula I may also be obtained by reacting a metal salt of the acid of formula II in a solvent such as acetone or methylethylketone with a halogen compound of formula:

 (V)

in which R is as hereinbefore defined and Hal is a halogen atom such as chlorine or bromine.

A further method of synthesis consists of reacting pyrocatechol with a compound of formula:

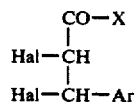 (VI)

in which Hal represents a halogen atom and Ar and X are as hereinbefore defined. This cyclisation reaction is preferably conducted in a hydroxylic solvent such as methanol in the presence of a condensing agent such as sodium methoxide. However it is also possible to operate in other solvents such as acetone in the presence of, for example, potassium carbonate.

The benzodioxan derivatives of formula I have interesting pharmacological properties and, according to the substituents present, have antiinflammatory, analgesic, antipyretic, antitussive, local anesthetic and antiarrhythmic activity, and inhibit the central nervous system. They can be administered topically, orally or by injection as suitable pharmaceutical formulations in solid, liquid or suspension form (e.g. as ointments, lotions, tablets, capsules, phials, (e.g. as ointments, lotions, tablets, capsules, phials, or syrups).

The following Examples illustrate the invention. The melting and boiling points are in degrees Celsius and not corrected. The identity of the substances and their purity was ascertained by elementary analysis of C, H, N (and halogens where present), infrared spectra, N.M.R. and U.V. 3-phenyl-1,4-benzodioxan-2-yl carboxylic acid and its ester were prepared by the method of V. Rosnati, F. Sannicolo and G. Pagani, Gazz Chim. Italiana 98

The following table summarizes certain pharmacological characteristics of various terms described in the application, terms the symbols for which have the following meanings:

LR 348 : morpholinoethoxyethyl (3-phenyl-1,4-benzodioxan-2-yl)-carboxylate, hydrochloride LR 349 : N,N-diethylaminoethoxyethyl (3-phenyl-1,4-benzodioxan-2-yl)-carboxylate, citrate LR 367 : N-(3-phenyl-1,4-benzodioxan-2-yl carbonyl)-isopropylamine LR 394 : N'-phenyl-N-(3-phenyl-1,4-benzodioxan-2-yl carbonyl)-piperazine.H$_2$0

LR 510 : N-(N',N'-diethylaminoethyl)-(3-phenyl-1,4-benzodioxan-2-yl carbonyl)-amine LR 518 : (3-phenyl-1,4-benzodioxan-2-yl)-carbohydroxamic acid LR 519 : N-(3-phenyl-1,4-benzodioxan-2-yl carbonyl)-morpholine LR 520 : N,N-diethylaminoethyl (3-phenyl-1,4-benzodioxan-2-yl)-carboxylate, citrate

| Compounds | Indicative acute toxicity, mouse DL$_{50}$ mg/kg (intraperitoneally) | Stretching from acetic acid, DE$_{50}$ mg/kg | Oedema from charragenin, rat, mg/kg % (i.p.) | Antipyresis, rat, mg/kg % | Antitussive activity DE$_{50}$ mg/kg | Antihistaminic activity, ileum of Guinea pig, γ/ml % | Local anaesthetic activity | | Arrhytmia CaCl$_2$-rat mg/kg (intravenously) | Activity on central nervous system, mouse mg/kg % (orally) |
|---|---|---|---|---|---|---|---|---|---|---|
| | | | | | | | tail of mouse DE$_{50}$ mg/ml | sciatic nerve of rat DE$_{50}$ mg/ml | | |
| LR 348 | 250 | 15.6 (8.4 – 28.8) | 50 = 40 | — | 50.0 (20 – 121) | 10 = 60 | 2.70 (1.82 – 4.00) | 12.2 (7.8 – 19.2) | — | — |
| LR 349 | 200 | 10 mg/kg = 20% | 50 = 50 | — | 39.5 (17-86) | — | 2.85 (1.44 – 5.64) | 11.2 (9.4 – 13.3) | — | — |
| LR 367 | >3000 | 138(75-255) | 200 = 30 | — | 86 (25-301) | — | — | — | — | depression of spontaneous motility, 150 = 32 |
| LR 394 | 330 | 22 (11-43) | 42 = 50 | 65 = 100 | 10 mg/kg = 64% | — | — | — | — | depression of spontaneous motility, DE$_{50}$ (mg/kg) 33.5 |
| LR 510 | 75 | — | — | — | — | — | — | — | — | Catalepsy (haloperidol) 15 = 33 |
| LR 518 | 175 | — | 40 = 12 | — | — | — | — | — | — | Potentiation of barbituric hypnosis 15 = 20 |
| LR 519 | 750 | — | 180 = 15 | — | — | — | — | — | — | Stereotipy (apomorphine) 40 = 30 |
| LR 520 | 300 | — | 60 = 9 | — | — | — | — | — | 7.5 = 40 | Stereotipy (amphetamine) 180 = 20 |

EXAMPLE 1

(3-phenyl-1,4-benzodioxan-2-yl)-carbohydroxamic acid

To 2.5 g of Na dissolved in 75 cc of absolute $CH_3OH$ is added a solution of 3.5 g of $NH_2OH.HCl$ in 50 cc of $CH_3OH$, and to this mixture are added, after filtering, 13.5 g of ethyl (3-phenyl-1,4-benzodioxan-2-yl)-carboxylate. The mixture is stirred for 30 minutes, the methanol is eliminated, and the residue is cooled and acidified with dilute $CH_3COOH$. The precipitate is filtered off and crystallized from ethyl acetate, m.p. = 203°–4°.

EXAMPLE 2

Morpholinoethoxyethyl (3-phenyl-1,4-benzodioxan-2-yl)-carboxylate

To a mixture of 13.3 g of methyl (3-phenyl-1,4-benzodioxan-2-yl)-carboxylate, 12.5 g of 2-($\beta$-morpholinoethoxy)ethanol and 215 cc of anhydrous heptane, heated to 100° C, a solution of sodium ethylate (obtained from 0.165 g of Na metal in 10 cc of absolute ethanol) is added in small portions. Heating is continued until the azeotropic ethanol-heptane mixture no longer distils. The reaction mixture is then evaporated to dryness. The residue is dissolved in $H_2O$ and extracted with diethyl ether. The organic phase is washed with $H_2O$ and dried over $Na_2SO_4$. The solvent is removed under vacuum, and the hydrochloride is prepared from the residual oil, m.p. = 162°–3° (from alcohol-ether).

EXAMPLE 3

N,N-diethylaminoethoxyethyl (3-phenyl-1,4-benzodioxan-2-yl)-carboxylate

To a suspension of 12.8 g of (3-phenyl-1,4-benzodioxan-2-yl)-carboxylic acid in 100 cc of $ChCl_3$, 5.1 g of triethylamine are added. The mixture is chilled and 5.4 g of ethyl chlorocarbonate are added dropwise. After stirring for 15 minutes, 8.8 g of N,N-diethylaminoethoxyethanol are added. After 2 hours the mixture is treated with water, the organic phase is separated and dried over $Na_2SO_4$. The solvent is removed under vacuum and the residue is transformed in the corresponding citrate (m.p. 73°–74°, from isopropanol).

EXAMPLE 4

N,N-diethylaminoethyl (3-phenyl-1,4-benzodioxan-2-yl)-carboxylate

To a suspension of 22 g of sodium (3-phenyl-1,4-benzodioxan-2-yl)-carboxylate in 100 cc of anhydrous acetone, 12 g of N,N-diethylaminoethyl chloride, dissolved in 20 cc of acetone, are added. The mixture is stirred for 2 hours. The sodium chloride formed is filtered off and the filtrate is evaporated to dryness. The citrate is prepared from the residual oil, m.p. = 99°–100° (from ethyl acetate).

EXAMPLE 5

N-isopropyl-(3-phenyl-1,4-benzodioxan-2-yl)-carboxamide

To 22 g of (3-phenyl-1,4-benzodioxan-2-yl)-carboxylic acid in 300 cc of anhydrous benzene are added 18.1 g of $PCl_5$ in portions with cooling. After 2 hours the reaction mixture is added to a cold solution of isopropylamine in anhydrous benzene. After stirring for 2 hours, the product is poured onto ice. The organic phase is separated, washed with $H_2O$ and finally dried over $Na_2SO_4$. The solvent is removed under vacuum. The residue is crystallised from isopropyl alcohol, m.p. = 196°–8°.

N-(3-phenyl-1,4-benzodioxan-2-yl-carbonyl)-morpholine, (m.p. = 148°–150°, from alcohol), is prepared in a similar manner.

EXAMPLE 6

N-(N',N'-diethylaminoethyl)-(3-phenyl-1,4-benzodioxan-2-yl)-carboxamide 10 g of methyl (3-phenyl-1,4-benzodioxan-2-yl)-carboxylate are added to 13 g of N,N-diethylethylenediamine in which 10 mg of Na metal have been dissolved. The mixture is heated in a current of nitrogen until all the methanol liberated by the reaction has distilled off. The excess amine is then removed under vacuum. The residue is crystallised from benzene-hexane, m.p. = 90°–2°.

N-benzyl-(3phenyl-1,4-benzodioxan-2-yl)-carboxamide (m.p. = 171°–2°, from $CH_3OH$) and N-phenyl-N'-(3-phenyl-1,4-benzodioxan-2-yl-carbonyl)-piperazine monohydrate (m.p. = 241°–2°, from alcohol-$H_2O$) are similarly prepared.

We claim:

1. A compound of the formula

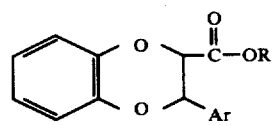

(I)

or a pharmaceutically acceptable salt thereof, in which Ar represents a monocarbocyclic substituted or unsubstituted aryl group, and R is an $\omega$-aminoalkyl, an $\omega$-aminoalkoxyalkyl radical or an $\omega$-aminoalkyl wherein the amino group is

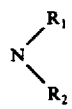

wherein $R_1$ and $R_2$ are identical or different, and are hydrogen, lower alkyl, or $R_1$ and $R_2$ are joined together to form an N,N-alkyleneimino, an N,N-oxoalkyleneimino, or an N,N-aza-alkyleneimino group in which the alkylene has three to eight carbon atoms.

2. A compound according to claim 1 in which Ar is phenyl, lower alkyl phenyl, trifluoromethyl phenyl, lower alkoxy phenyl, halogen phenyl.

3. A compound according to claim 1 which is morpholinoethoxyethyl (3-phenyl-1,4-benzodioxan-2-yl)-carboxylate.

4. A compound according to claim 1 which is N,N-diethylaminoethoxyethyl (3-phenyl-1,4-benzodioxan-2-yl)-carboxylate.

5. A compound according to claim 1 which is N,N-diethylaminoethyl (3-phenyl-1,4-benzodioxan-2-yl)-carboxylate.

* * * * *